United States Patent [19]

Alt

[11] Patent Number: 5,411,527
[45] Date of Patent: * May 2, 1995

[54] DIFIBRILLATION ELECTRODES AND IMPLANTATION

[75] Inventor: Eckhard Alt, Ottobrunn, Germany

[73] Assignee: Intermedics, Inc., Angleton, Tex.

[ * ] Notice: The portion of the term of this patent subsequent to Sep. 1, 2009 has been disclaimed.

[21] Appl. No.: 937,173

[22] Filed: Aug. 31, 1992

Related U.S. Application Data

[63] Continuation-in-part of Ser. No. 517,186, May 1, 1990, Pat. No. 5,143,089.

[51] Int. Cl.$^6$ .............................................. A61N 1/05
[52] U.S. Cl. ........................................ 607/5; 607/120; 607/122; 607/123; 607/129; 128/642
[58] Field of Search .................. 128/639–642, 128/644, 784–786, 419 P, 419 D; 607/5, 120, 122, 123, 129

[56] References Cited

U.S. PATENT DOCUMENTS

| | | | |
|---|---|---|---|
| 4,112,952 | 9/1978 | Thomas et al. | 128/785 |
| 4,281,668 | 8/1981 | Richter et al. | 128/784 |
| 4,417,581 | 11/1983 | Dawson | 128/642 X |
| 4,548,203 | 10/1985 | Tacker, Jr. et al. | 128/784 X |
| 4,567,900 | 2/1986 | Moore | 128/784 |
| 4,574,814 | 3/1986 | Buffet | 128/786 |
| 5,053,048 | 10/1991 | Pinchuk | 128/DIG. 21 |
| 5,103,837 | 4/1992 | Weidlich et al. | 128/784 |
| 5,143,089 | 9/1992 | Alt | 128/642 X |
| 5,203,348 | 4/1993 | Dahl et al. | 128/784 |

FOREIGN PATENT DOCUMENTS 1219017  1/1971  United Kingdom ................ 128/784

OTHER PUBLICATIONS

Starrenburg et al, "Carbon Fiber as an Electrode Material", IEEE Trans BioMed Ing., vol. BME-29, No. 5, May 1982, pp. 352–355.

Newsweek, "New Plastics That Carry Electricity" Jun. 18, 1979, pp. 77–78.

*Primary Examiner*—Lee S. Cohen
*Attorney, Agent, or Firm*—O'Connor Cavanagh Anderson Westover Killingsworth & Beshears

[57] ABSTRACT

An electrical lead has a cardioverting/defibrillating electrode composed of a multiplicity of tiny flexible elongate metallic fibers, for implantation in a patient. One embodiment of the lead is implanted by puncturing the chest/abdominal wall of the patient and inserting the lead, fiber electrode first, into the body through the puncture site followed by maneuvering the lead by endoscopy to position the electrode adjacent the epicardium of the heart for electrical interaction with the ventricles. The fibers may be interwoven to form a thin tube prestressed to assume a flat spiral shape to permit it to be straightened with a stiffening wire for maneuvering to return to its flat spiral shape after proper positioning and removal of the wire. In other embodiments, the lead has multiple conductors electrically connected to respective electrodes arranged on the lead for positioning transvenously relative to selected regions of the heart. For ventricular fibrillation, the arrangement is such that one electrode is positioned in the right ventricle and another in either the subclavian vein or pulmonary artery at the left side of the heart when the lead is fully implanted. For atrial fibrillation, the arrangement is such that one electrode is positioned in the right ventricle and another in the pulmonary artery adjacent the left atrium when the lead is fully implanted. The fibers of the electrode have a surface layer composed of electrically conductive carbon which may include a substance to inhibit thrombosis, inflammation and/or coagulation at the exposed surface of the electrode when the lead is implanted in the patient's body.

31 Claims, 4 Drawing Sheets

FIG. 9
VENTRICULAR DEFIB.

FIG. 9A
ATRIAL DEFIBRILLATION

DIFIBRILLATION ELECTRODES AND IMPLANTATION

CROSS-REFERENCE TO RELATED APPLICATION

This application is a continuation-in-part of the U.S. patent application Ser. No. 07/517,186 of the same inventor, filed May 1, 1990, now U.S. Pat. No. 5,143,089, issued Sep. 1, 1992 ("the '089 patent").

BACKGROUND OF THE INVENTION

The present invention relates generally to methods and apparatus for therapeutic treatment and/or monitoring of functions of the human or animal body, in part by means of the efficient transmission or delivery of electrical signals between a therapeutic or monitoring system, such as an automatic implantable cardioverter/-defibrillator, and the tissue or blood of the body, such as that of the heart, via one or more implanted electrodes. More particularly, the invention is directed to improvements in the configuration, energy transfer efficiency, therapeutic and sensing effectiveness, and implantation techniques of such implantable electrodes, which in certain preferred applications are composed of carbon fibers or carbon-coated metallic fibers, for purposes of stimulating or sensing electrical reactions in body tissue and especially heart tissue.

As is observed in the '089 patent, the rapidly advancing state of the art of microelectronics has led to considerable progress in medical technology owing in great part to microminiaturization of electronic components and the consequent markedly reduced size of medical devices utilizing such components. This is particularly significant in the case of implantable medical devices of the types adapted to monitor and/or deliver electrical indicia and/or stimuli (broadly, electrical signals) within the body for the purpose of detecting or stimulating various selected biological processes. The devices of interest here are implantable and external defibrillators, which broadly include devices capable of monitoring and controlling cardiac activity as necessary to detect and alleviate arrhythmias or dysrhythmias such as fibrillation (both atrial defibrillation (AF) and ventricular fibrillation (VF)), pathologic tachycardia, and, in some of the multi-function devices, even bradycardia. In principle, these devices respond automatically to the sensing of the dysrhythmia of interest to restore normal, regular cardiac rhythm by delivering electrical stimuli in the form of pulses or shocks to the atrial or ventricular cardiac tissue, as appropriate.

Typically, the automatic defibrillator is implanted just beneath the flesh in the patient's abdomen or pectoral region, but the associated defibrillating or cardioverting electrodes have required implantation by a surgical procedure (thoracotomy) by which the chest cavity of the patient is opened to expose the heart and allow the electrode(s) to be secured directly to the epicardium or the pericardium. For example, one or more defibrillating patch electrodes of considerable surface area may be placed externally in stimulating relation to the myocardium so that an electric field may be established through the heart. Rather than applying patch electrodes in such a way that the electric field extends from one side of the heart to the other, usually through the ventricles, the epicardial patch or patches may be implanted to react with an endocardial counter-electrode implanted transvenously in the superior vena cava or further into the atrium or ventricle on the right side of the heart. The patch electrode(s) may be sutured directly to the epicardium after opening the pericardial sac. The implantation of electrodes external to the heart by the thoracotomy procedure is obviously highly traumatic to the patient, especially those with the very cardiac dysfunction it is intended to alleviate, and also necessitates considerable in-hospital recovery time for the patient.

Aside from risks and complications associated with the need for general anesthesia in such procedures, the electrode placement and accompanying thrombosis have tended to produce inefficient transfer of electrical energy between the body tissue and blood and the pulse generator of the defibrillator. Such inefficiency and the short to medium term increases in energy threshold commonly encountered with electrode implantation often combine to produce an inadequate result; that is, to retard the delivery of sufficient energy across the electron-ion interface, within the electrical energy capacity of the implanted and necessarily battery-powered device, to provide consistent and reliable defibrillation. As this is the primary function of the device, it becomes necessary to remove and replace the battery-depleted device (usually not exhausted but of inadequate stored energy), perhaps at altogether intolerably frequent intervals, with the attendant physical and psychological impairment of the patient.

Additionally, defibrillator implant patients have suffered inadequate healing, infection, pericardial hematomas and other trauma as a result of the surgical procedure, and some have experienced a further deterioration of the pumping function of the heart which is attributed to the sewn-on epicardial patch electrode. A survey of the various complications is treated in an article by D. Echt et al. titled "Clinical experience, complications and survival in 70 patients with the automatic implantable cardioverter/defibrillator", in *Circulation*, vol. 71, no. 2, 1985, pp. 289 to 296.

Prior art of interest is described in the following patents: in U.S. Pat. No. (USPN) 4,548,203, two pairs of spaced electrodes on the myocardium to control VF and tachyrhythmia at different times; in U.S. Pat. No. 4,481,953, an endocardial electrode with electrical connection between different low resistance conductors; in U.S. Pat. No. 4,355,646, an electrode arrangement for measuring impedance changes in the ventricle and for cardioversion using an endocardial electrode with two electrode points in each of the atrium and the ventricle connected by a low resistance triaxial lead to an implanted cardioverter or defibrillator; in U.S. Pat. No. 4,355,642, a disk electrode for sensing cardiac activity and for use in defibrillation; in U.S. Pat. No. 3,738,370, use of a bipolar coaxial catheter for defibrillation; in U.S. Pat. No. 4,708,145, an epicardial pad electrode and opposite endocardial electrode sequentially energized for defibrillation; in U.S. Pat. No. 4,787,389, endocardial and epicardial electrodes used for defibrillation and antitachycardia with means to prevent the antitachy pacemaker from damage by the defibrillating pulses; in U.S. Pat. No. 4,774,952, a multiple electrode structure concentrates current in selected areas of the heart during defibrillation. Other literature of interest includes Soviet author's certificate 1,263,260 with multi-electrode structure for even disposition about the heart to reduce current damage of myocardial cells; and British application 2,182,566, in which a disk electrode's elasticity permits it to conform to the heart's movements.

Further patents of interest include U.S. Pat. Nos. 4,270,549 and 4,291,707, in which a patch electrode is applied to the myocardium, a fine titanium wire structure is used as an electrode pole, and the mean current density is increased by using lateral insulators, and in which the patch electrode is applied without opening the chest cavity, by means of a spatula-like instrument introducible into the chest cavity through a cut, but of sizable dimensions—four to six centimeters (cm) wide and 1 to 3 cm thick—as to still require somewhat complex surgical procedures and use of general rather than local anesthesia.

Other patents representative of the state of the art in defibrillation and implantable defibrillating electrodes include U.S. Pat. Nos. 4,765,341 to M. Mower et al. and 4,512,351 to P. Pohndorf, and European application No. 0317490 of T. J. Fogarty published May 24, 1989 claiming U.S. priority date of Nov. 13, 1987.

Despite these proposals and some advances, problems have persisted in attempts to interface electrodes with body tissue to attain a combination of low resistance conductivity, large surface area, low polarization and low intrinsic stiffness, while providing long-term communication of electrical signals and relatively high current levels. Further, the implantation and manipulation of the prior art electrodes have remained complex procedures, and the methods and apparatus employed for defibrillation have not been entirely successful owing principally to inefficient energy transfer between the electrode and excitable tissue (i.e., tissue having cell membrane field strength which can be stimulated electrically to produce cell depolarization).

Energy transmission and transfer between pacemaker electrodes and the heart has received considerable attention. The reader's attention is invited, for example, to a survey article by Ripart and Muciga titled "Electrode heart interface: definition of the ideal electrode", in *PACE*, vol. 6, March 1983, pp. 410–421. Although there, some encouraging results were obtained using low polarization materials such as platinum, iridium and pyrolyzed carbon in the electrode tip having average surface area of 10 mm$^2$ (square millimeters), for stimulation with pacing pulses ranging from 2.5 to 5.0 volts, and for sensing cardiac activity, cardiac pacing electrode requirements are manifestly different from defibrillation electrode requirements, the latter involving application of shocks with amplitudes of up to many hundreds of volts and over electrode surface areas of perhaps 10,000 mm$^2$.

German Democratic Republic patent 26 32 39 of Oct. 30, 1987 discloses a pacing lead composed of a bundle of anisotropic carbon fibers. Such an electrode may be effective for pulse transmission along its longitudinal axis, but its relatively tiny point contact surface areas at the tissue interface and tendency of the electrode interface to erode over time would render it incapable of providing the large surface area required for defibrillation. The transfer of adequate energy from defibrillating pulses of from 500 to 2,000 volts typically requires patch electrode surface area of from 50 to 100 cm$^2$ (square centimeters) to avoid possible local burning of the tissue, and transvenous electrode surface area of from 4 to 20 cm$^2$ for uniform energy flow through the heart.

It is highly desirable that the defibrillating electrode have characteristics of low energy consumption, low polarization, flexibility to avoid mechanical restriction of movement of the heart during beating, and ease of implantation. It is further desirable that the defibrillating electrode be readily adapted for implantation without need for a thoracotomy and all its risks, patient recovery time, pericardial hemorrhaging, potential infection, and other complications such as those attributable to adhesions from prior surgery where the patient is undergoing electrode replacement. In addition to its advantages by way of reducing trauma and in-hospital recovery time, simplified implantation would reduce hospital costs otherwise associated the need for specialized open heart surgical facilities and attending personnel.

The invention disclosed in the '089 patent provides an improved lead assembly for biomedical use in stimulating and/or sensing electrical phenomena in relation to excitable tissue of the body. The electrode of the lead assembly is conductively connected to an electrical lead and is composed in principal part of flexible non-metallic electrically conductive fiber strands. The fibers possess substantially isotropic conductance characteristics to form an improved electrical interface with body fluid (e.g., blood) and/or excitable tissue when the lead assembly is implanted into the body. Specifically, the electrode characteristics improve the energy transfer and consequent electrical communication across the electron-ion interface between the electrode and the blood/tissue. This interface is formed along the entire length of exposed (uninsulated) surface of each fiber, rather than at restricted point contact areas. The isotropic property of the fiber material assures that it will conduct electrons substantially equally in all directions, thereby considerably expanding the electron-ion boundary which is otherwise substantially limited to such virtual point contact at the ends of the fibers in theretofore proposed carbon fiber electrodes. The electrode is intentionally constructed to provide a considerable length of uninsulated fiber surface to form the interface.

The '089 patent invention also provides a multiplicity of such fibers in the composition of the electrode of the lead assembly, which, together with the substantially isotropic conductance characteristic or property of each fiber and the exposure of a substantial length of the fibers in the electrode, presents an effective surface area which is much larger, indeed many times larger, than the apparent actual surface area of the electrode calculated from its linear dimensions. That invention also resides in a technique by which the fibers are held together to provide an electrode configuration having a size and shape adapted to form the desired interface according to the intended implant location of the electrode in the body. For example, the fibers may be woven in strands which themselves are interwoven to form two- or three-dimensional configurations especially suited as defibrillation electrodes. Further, the invention of the '089 patent provides methods of shaping and implanting such electrodes for various biomedical applications, including use with implantable automatic defibrillators.

The principal advantage of lead assemblies incorporating such electrodes over the prior art is the efficiency of energy transfer across the electrical interface at the electron-ion boundary between the flexible fiber electrode configuration and the body fluid and/or excitable tissue in contact with or in the immediate vicinity of the interface, both in terms of the proportion of electrical energy applied to the interface which is delivered across the interface, and the speed with which this delivery occurs. This is a function of the nature of the interface provided by the electrode in the lead assembly—low polarization, low capacitance, low resistance and low impedance—and the effective (in contrast to actual) surface area of the interface. Such advantages are particularly important in the case of implantable battery-powered medical devices, where wasted energy can cause rapid depletion of the batteries and consequent shorter intervals between surgical replacements. Worse, the battery depletion may render the device incapable of functioning properly in a life-threatening situation, such as in the case of a defibrillator implanted in a patient experiencing VF.

Tests have demonstrated that the energy yield (energy transfer) attained with an electrode of the type disclosed in the '089 patent, used for delivery of defibrillating shocks, is at least about 30% greater than that achieved with prior types of electrodes. Accordingly, successful defibrillation is much more likely at relatively lower levels of energy deliverable from the device, with the improved electrode. These tests have also shown that the integral of the pulse during even the first millisecond is about 50% greater (i.e., a much faster rise time for the delivered impulse of electrical energy) compared to lead assemblies with the best prior art electrodes, for the same absolute energy input. For example, a time interval of about 4-½ milliseconds was required to develop 14 joules of energy across the interface with a 30 joule input for conventional metal defibrillating electrodes, whereas electrodes fabricated according to the invention disclosed in the '089 patent yielded 22.6 joules for the same input and the same time interval.

The carbon fibers provide the electrode with a flexible configuration capable of conforming in shape and size to the region of tissue with which it is to interact, and allow the electrode to undulate with movements of the tissue such as during defibrillation. The fibers may be held together without bonding or other material which otherwise might to some degree adversely affect the size of the electrode's effective surface area relative to its apparent actual surface area for energy transfer.

The prior art relative to the invention disclosed in the '089 patent further includes:

U.S. Pat. No. 4,574,814 to Buffet, where an axially slidable coaxial probe provides contact in both atrium and ventricle in the form of carbon fiber feather dusters of variable separation for synchronous pacing in chambers of different size. The resiliently deformable fibers assume the feather duster shape when unrestrained, with the fiber ends providing an envelope of contact with myocardial tissue to increase the area of anchoring, and with reliance on end contact (point contact) of non-isotropic fibers with the tissue for excitation and anchoring.

An article by Starrenburg et al. titled "Carbon Fibers as an Electrode Material" in *IEEE Transactions on Biomedical Engineering*, vol. BME-29, no. 5 (May 1982), at pp. 352 et seq., which describes a flexible carbon fiber bundle electrode having a short segment of straight bare fibers between two insulated regions for muscle stimulation when implanted in the wall of the small intestine of a dog, but in which the carbon fiber electrode suffered breakdown during electrical pulse testing in a bath and as a result of mechanical stresses when implanted.

An article titled "New Plastics That Carry Electricity" in the Jun. 18, 1979 issue of *Newsweek* magazine, where polyacetylene plastic doped with chemicals to add free electrons are described for carrying electric current. The suggested uses include pacemaker lead wires, but no suggestion of forming the plastics into fibers or strands or of weaving fibers together or as fiber electrodes.

Great Britain patent No. 1 219 017 to Thomson Medical-Telco, in which an electrical conductor of braided carbonized fibers forms a lead for cardiac pacing, and is insulated along its entire length except at the very end to permit point contact excitation of tissue. The material is non-isotropic, of high resistivity for current flow in the direction of tissue or blood at the longitudinal surface of the fiber compared with the end point.

U.S. Pat. No. 4,506.673 to Bonnell describes electrical tissue growth stimulators using biodegradable electrically conductive carbon particle-impregnated cotton fibers in a non-isotropic mesh for cathodic and anodic stimulation.

U.S. Pat. No. 4,198,991 to Harris, in which a cardiac pacing lead uses carbon filaments covered with an insulating sheath except at the lead tip as a brush-like electrode structure for point contact of tissue.

SUMMARY OF THE INVENTION

According to an aspect of the present invention, a patch, tube or other mesh of individually woven isotropic carbon fibers or metallic fibers coated with isotropic carbon is employed as an electrode for cardioversion or defibrillation. The electrode may also be impregnated with an anticoagulant substance or pharmacologic agent, such as heparin or hirudin, to prevent blood clotting or platelet formation along the fibers. Heparin or heparinic acid is a natural anticoagulant substance found in various tissues such as in the liver and lungs of man and other mammals. In conjunction with the heparin cofactor, it acts as an antithrombin and an antiprothrombin to prevent platelet agglutination and consequent thrombus formation. Hirudin is an antithrombin substance which is extracted from the salivary glands of the leech, and has the property of preventing coagulation of the blood. Thrombin is an enzyme formed in blood when shed or subjected to a foreign body, that converts fibrinogen into fibrin. It causes thrombosis, which is clotting and the potential for infarction of tissues supplied by the blood and the buildup of scar tissue.

The impregnated coating prevents thrombosis to avoid formation of fibrous tissue which would otherwise decrease the efficiency of the electrode in energy transfer vis-a-vis the cardiac tissue to be stimulated. This tends to assure that the electrode surface remains exposed to the blood and/or tissue, and avoids imposing a need for a defibrillating or other electrical impulse to cross and be partly dissipated in a fibrous tissue "scar" during stimulation of the heart, for example, or a loss of sensitivity to electrical impulses arising from electrical cardiac activity when the electrode is used for sensing. Additionally or alternatively, dexamethasone or other steroids or steroid drugs may be applied to the individual fibers to prevent scar formation on the electrode.

U.S. Pat. No. 4,577,642 to Stokes, for example, proposes coating an electrode with an anti-inflammatory drug to prevent cell proliferation at the tip and thereby promote a better electrical interface, but the purpose and the manner in which it is achieved are different from this aspect of the present invention.

Therefore, it is an object of the invention to provide an improved long term, low threshold defibrillating electrode comprising isotropic carbon or carbon-coated metallic fibers impregnated with an antithrombin or anticoagulant agent or an anti-inflammatory substance such as asteroid.

According to another aspect of the invention, an isotropic carbon or carbon-coated metal fiber defibrillation electrode is particularly suited for minimal invasive implantation by surgically implanting it through a puncture opening in the abdomen or chest wall. The electrode may be inserted, using a puncture needle and an associated introducing catheter, into the pericardial sac for positioning adjacent the epicardium. Percutaneous endoscopic implantation of an automatic implantable cardioverter/defibrillator (AICD) lead has been proposed in the literature but the implanted lead was outfitted with an AICD patch, not a braided carbon or metal fiber mesh material or a plurality of tubular carbon or metal mesh fibers which may be advanced around the heart with a predetermined placement, as in the present invention. The aforementioned European application No. 0317490 of T. J. Fogarty is also of interest in this respect.

Accordingly, it is another important object of the present invention to provide improved techniques for surgically implanting electrodes, and particularly conductive fiber electrodes which are most especially adapted for such procedures, for defibrillation or for other electrically excitable tissue stimulation or sensing purposes.

A flat coil electrode is the presently preferred configuration for puncture implantation according to the invention. The tubular braided conductive fibers (carbon or carbon-coated), preformed into the coil configuration, are inserted through the puncture using a stiffening wire.

A further object, then, is to provide an implantable conductive fiber electrode which is prestressed to possess a flat coil or spiral shape, so that after introduction and proper positioning during an implant procedure in which the fiber is constrained to a straight configuration, it will return to the spiral shape for desirable coverage of a large area of the tissue to be stimulated.

Another aspect of the present invention resides in providing an improved transvenous electrode system for defibrillation. According to the invention, a coaxial arrangement is provided in which an electrode arranged to be positioned in an upper thoracic vein and another in the right ventricle are assembled within a single lead, with the tip of the lead used for sensing, in either a bipolar or a unipolar electrode configuration.

Another important feature of the present invention is to provide improved electrode position for more effective energy pathways in purely transvenous defibrillation of the atrium or of the ventricle or of both by positioning one electrode in the pulmonary artery—preferably the left pulmonary artery, and another electrode within the right ventricle. Additionally, a third electrode may be placed in one of the upper thoracic veins, whereby the right ventricle electrode functions as a cathodal pole, and the pulmonary artery and thoracic vein electrodes form two anodal poles. The vectorial arrangement of right atrial electrode position and pulmonary artery electrode position guarantees the optimum electric vector (path of current) for atrial defibrillation in case of atrial flutter/fibrillation with respect to ease of application and implantation, especially if a single lead incorporating both electrodes is used.

Using braided carbon fiber or carbon-coated metallic material a tripolar electrode lead may be provided in which the tip and the inner coil are used for pacing and sensing of the right ventricle, the fiber electrode with its large effective surface area is the second electrode conductively connected in the right ventricle, and a third electrode for defibrillation in the upper thoracic vein is conductively connected to the implantable defibrillator. The electrically conductive fiber material, whether carbon or carbon-coated, does not require a large diameter for large surface area, owing to creation of that surface from many tiny woven strands. Accordingly, a single lead may be fabricated which is capable of sensing and pacing as well as defibrillating, and which may selectively produced in unipolar, bipolar or even tripolar configuration. A common ground may be used against the tip for sensing and pacing of the heart, or a reference point may be provided to produce a narrower vector for the electric field with less likelihood of sensing noise which could overwhelm or at least impede detection of the desired electrical cardiac signal.

Another object of the invention is to provide tuning or matching of the characteristics of the output circuit of the defibrillator pulse generator to those of the lead-/electrode system. Characteristics of pulse width, pulse duration, pulse amplitude, pulse shape and current flow generated by the discharge capacitors of the defibrillator are matched to the low impedance properties of the lead/electrode system, for optimum energy transfer and efficiency.

BRIEF DESCRIPTION OF THE DRAWINGS

The above and still further objects, aspects, features and attendant advantages of the present invention will be better understood from a consideration of the following detailed description of a presently preferred embodiment and method thereof, taken in conjunction with the accompanying drawings, in which.

DESCRIPTION OF THE PRESENTLY PREFERRED EMBODIMENTS AND METHODS

The features of the invention primarily reside in new and improved electrode structures, improved lead/electrode assemblies and electrode arrays and arrangements for transvenous cardioversion/defibrillation, improvements in surgical techniques and procedures by which such structures, assemblies and arrays are implanted, and techniques for matching the output characteristics of the defibrillator or other implantable medical interventional device to the electrical characteristics of the lead/electrode assembly.

The electrode structures are typically employed as part of an implantable lead assembly for biomedical use in a living body to stimulate and/or sense electrical excitation of selected excitable tissue in the body when the lead assembly is implanted. Such lead assemblies are conventionally provided with an electrically conductive lead to which an electrode is conductively connected at the distal end of the lead. In the case of the fiber electrode structures of the invention, the electrode provides a low polarization, low capacitance, low resistance and low impedance electrical interface with contacting body fluid and/or adjacent excitable tissue. The electrodes of principal interest are fabricated from a multiplicity of uninsulated, individual, substantially isotropic electrical current conducting fibers, which are maintained in a flexible configuration adapted to form the electrical interface along an entire substantial length of electrically uninsulated surface of the configuration. Such configurations are shaped and sized to be easily positioned at the selected site of the electrical interface when the lead assembly is implanted in the patient's body. As pointed out above, a multiplicity of interwoven fibers provide an effective surface area for the electrical interface which is considerably greater than the apparent actual surface area of the overall electrode configuration as determined strictly from its linear dimensions.

The flexibility of such configurations is preferably maintained in principal part by the fibers themselves, by the interweaving of the fibers. The interweaving may be performed to produce substantially two-dimensional or three-dimensional shapes. The substantially isotropic, electrically conductive carbon, carbon derivative or carbon-coated metallic fibers preferably have thicknesses less than about 40 microns (i.e., micrometers, or $10^{-6}$ meter).

Electrically conductive polymers are described, for example, by Dr. Herbert Naarmann of BASF in "Elektrisch leitfahige Polymere: Anwendungsspektrum noch nicht ausgereizt ", *Chemische Industrie*, no. 6/87, and in "Die elektrochemische Polymerisation", *Angewandte Makromolekulare Chemie* 162, 1988, pp. 1–17. U.S. Pat. No. 4,468,291 describes a method for producing electrically conductive polypyrrole films.

Among the materials useful for fabricating the fiber electrodes are iodine-doped polyacythylene fibers, which have a conductivity of more than 100,000 siemens per cm, sometimes with a high degree of crystallinity; polypyrrole polymer; and carbon or C fibers obtainable from the Celion Company with diameters of 20 microns as thin fiber strands which may be woven together.

In these electrically conductive carbon derivatives, the addition of electron donors or acceptors and the reduction of oxidation of the matrix produce a transition from electrically insulative to electrically conductive properties, with a perceptible increase in electron mobility and conductivity. These polymers have conductivities of up to 100,000 siemens per centimeter and possess the property of producibility in very fine fibers, with thinness in the range from 8 to 20 microns. A bundle of these small diameter fibers presents a very large effective surface area—for example, 10 $cm^2$ per cm of bundle length for a fiber bundle 2 millimeters in diameter with individual fibers of 12 microns thickness. Such a fiber bundle of only one cm in length could thus replace a defibrillation patch electrode having a surface area of 10 $cm^2$. Of course, for purposes of defibrillation, a one cm long fiber bundle would be impractical for application to the myocardium; instead, one or more such fiber electrodes having a length of, say, 10 to 15 cm could be used in the pericardial cavity to provide an effective total surface area of 100 to 150 $cm^2$ assuming all individual fibers were exposed. Although such effective surface area efficiencies not fully achievable in practice, the fluid present in the pericardial space assists in increasing the effective surface area of the fiber bundle to a figure considerably greater than the surface area measured geometrically by direct application to the myocardium.

Such electrically conductive polymers are flexible, and are biologically inert because of their carbon composition. Further, they exhibit a smooth exterior surface and possess reasonable non-thrombogenic characteristics which tend to reduce foreign body reaction, as has been confirmed in use of other types of carbon implants, as in bone surgery. The fibers are readily formed in a variety of suitable configurations, such as woven together, formed into a netting, or woven into small chains, bundles or tubes, in which the woven configuration provides desirable elasticity which allows movement with and conformance to the shape of the heart or other organs of interest.

Rather than carbon or electrically conductive polymers of this type, use may be made of metallic fibers of diameters in the range of, say, 10 to 30 microns, to create the desired large effective surface area electrodes. A suitable metallic electrode fiber, for example, is iridium platinum multistrand wire composed of nine strands of 0.0011" (about 27 microns) 10% iridium–90% platinum bare wire available from Sigmund Cohn Corp. of Mount Vernon, N.Y. as part number 10Ir9/49B. The multistrand wire may be braided to form larger bundles, or tubes or meshes.

Preferably, the metallic fibers or strands are coated with carbon to coating thicknesses starting as low as molecular layers in the nanometer range and up to about 10 microns. This provides the fibers with features and characteristics similar to those of the pure carbon polymer fibers described above, but with the distinct advantage that solid electrical connection is readily made between these coated metallic fine fibers and a low resistance, conductive lead wire (DBS wire, for example) by electro-welding, with only about 0.3 ohms per contact, to carry the defibrillation energy to the braid. A carbon material suitable for use in such coating is polyvinyl pyrrolidone, which can be applied to the metal strands or fibers by electro-galvanization or other suitable process such as that disclosed in German patent application P 36 07 302.4. Applying a carbon coating using an electrolytic process allows the thickness to be carefully controlled, according to such factors as length of time in the bath, magnitude of current, and so forth.

The DBS conductive wire lead may be formed into a helical coil which provides a central opening for a stylus. An uninsulated portion of the wire is brought into electrical contact with a portion of the braid from which the carbon is removed, thereby exposing the metal fibers, which may then be electrically welded to the lead. Molded silicone insulation is then applied over the junction to prevent moisture from penetrating. The benefits of good electrical connection by virtue of the metal to metal contact and electro-welding, together with the large effective surface area of the electrode and consequently permissible small actual size of the lead (4 or 5 french), exceed those of the fibers composed purely of the carbon derivatives. This is primarily because the polymer fibers must be crimped, the contact pressure is critical, and they cannot be welded. The electrical connection to the latter type of fibers can be made by application of a conductive epoxy which makes contact with the carbon.

In tests conducted to determine the electrical properties of electrodes composed of such fibers or fiber bundles of carbon, metal or metal/carbon, comparison was made of electrical energy transmission achieved using conventional defibrillation electrodes and using the fiber electrodes employed according to the invention. The electrodes were placed in a glass cylinder filled with saline solution, and various electrical energies were transmitted between the electrode of interest and an opposite electrode, and measurements were taken for the sake of comparison. The conventional electrode configuration used for the tests included a defibrillating patch electrode 6 cm long and 4 cm wide juxtaposed with an opposite electrode, while the fiber electrode configurations were fiber bundles, or woven fiber tubes or patches juxtaposed in each instance with an opposite electrode. The time slope of both the voltage curve and the current curve were recorded and the energy yield in terms of energy released by the defibrillating electrode to the water bath was calculated from the integral of these curves. It was found that a 20% to 30% energy yield increase was achieved using an electrode configuration consisting of a bundle of fine synthetic fibers of the type described above having a bundle thickness of two millimeters and a length of 10 cm, compared to the aforementioned conventional patch electrode. The maximum achievable voltage for a given energy level was also found to be greater with the fiber electrode than with the conventional patch electrode. The low polarization of the fiber material contributes to this achievement along with the large effective surface area of the electrode structure. Fiber patch electrodes also demonstrated improved energy yields (by about 20%) compared to similarly sized conventional flat patch electrodes. Low polarization (low capacitance) also contributed to improvement in critical rise time of the impulses attained in the energy transfer.

For use in defibrillating the heart, the fibers are interwoven to form a substantially flat patch electrode for positioning adjacent the epicardium or a tubular electrode for transvenous insertion within the heart. Preferably, the interwoven fibers of the tubular transvenous electrode cross over and under each other to enable expansion and contraction of the overall configuration with movements of the heart, so as to strengthen the electrode against fatigue during long term use for defibrillation.

In generalized therapeutic treatment of the patient, the flexible fiber electrode and associated current-carrying lead of the lead assembly are implanted as part of the overall automatic implanted cardioverter/defibrillator. This device includes a separately cased waveform or stimulus generator from which electrical impulses are transmitted through the lead to the electrode at one side of the electron-ion interface with surrounding blood and tissue. Electrical energy is delivered to the other side of the interface with rapid initial rise times as a consequence of the electrical characteristics of the interface. In the specific case where the therapeutic treatment is defibrillation of the heart, when ventricular fibrillation is detected a defibrillating impulse is applied to the proximal end of the lead to deliver a high energy shock to the heart with optimum efficiency across the electron-ion interface at the electrode positioned adjacent the epicardium.

Energy transmission investigated in animal tests also produced improved results using the fiber electrode configuration. For example, a pig's heart was successfully defibrillated using such an electrode inserted into the pericardial space between the pericardium and the myocardium, with only half the energy required to defibrillate using a conventional defibrillating patch electrode.

Electrodes produced from such electrically conductive, carbonized polymer or metallic or carbon-coated metallic fibers may be used for sensing electrical signals generated in biological tissue as well as for electrically stimulating such tissue. When the tissue cells are depolarized they generate small electrical signals with voltage levels in the millivolt range. The signals sensed by the electrode on or in the heart may be delivered via a lead to the sense amplifier circuitry in the implanted stimulus generator of the medical device. In such arrangements, it is important that the electrode-to-body tissue interface exhibit high electrical conductivity. The sensed signals may be processed such as by amplification and filtering, for example, and then used to control an implanted or external therapeutic device.

Figures 1, 2, 3, 4:
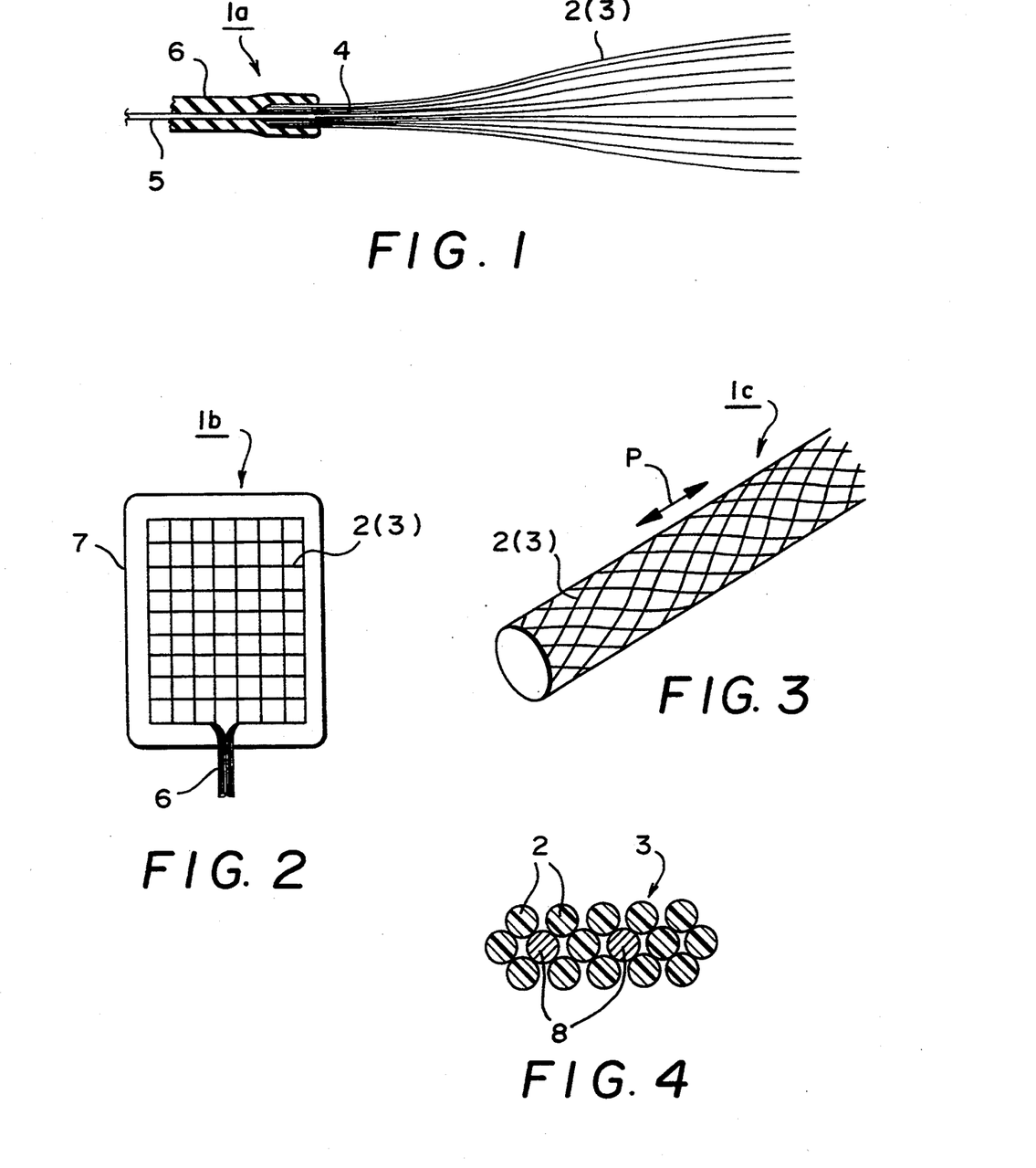
FIG. 1 is a side view, partly in section, of a fiber electrode including isotropically conductive fibers, according to the invention.
FIG. 2 is a plan view of a two-dimensional patch or pad electrode woven from fibers.
FIG. 3 is a perspective view of a portion of a three-dimensional tubular electrode woven from fibers.
FIG. 4 is a cross-sectional view of a fiber bundle electrode in which some of the fibers are markers opaque to X-ray or fluoroscopic radiant energy.

Various embodiments of the fiber electrode and other components of therapeutic systems or devices are illustrated in the Figures, and are not intended to be shown to scale. In FIG. 1, fiber electrode 1a includes a plurality of electrically conductive fibers 2 or fiber strands 3 (shown in cross-section in FIG. 4) which are compacted together at one end to form a short rod-like configuration 4 for electrical connection to an electrical lead 5. Electrical insulation 6 surrounds the point of connection and extends about substantially the entire length of the lead except for the proximal end which is to be connected to implanted therapeutic medical device 19 (FIG. 6) such as an automatic cardioverter/defibrillator.

At points of the electrode 1a departing from the rod-like portion 4 (FIG. 1), the fibers 2 or strands 3 are not compacted together but are free to separate from one another so that they may fan out to provide a larger effective area of electrical interaction with blood and/or excitable tissue at the distal end of the overall lead 6 (including the electrode). This larger area of interaction is attributable to the multiplicity of fibers each having its own surface area, and in part to the isotropic property of the electrode fibers in which each fiber is capable of conducting radially along its entire length, and thus of interacting electrically with excitable tissue over that entire length rather than being restricted to interaction with tissue at the distal endpoint of the respective fiber.

FIG. 2 illustrates a flat two-dimensional patch or pad electrode 1b which is woven with bundles of fibers having a plurality of individual fibers 2 or strands 3, as in FIG. 4. The electrode fibers are electrically connected to the distal end of the electrical conductor of insulated lead 6. The netting or mesh formed by the woven fibers is applied to a flexible electrically insulating carrier 7 which provides electrical insulation on one surface of electrode 1b and an insulative rim about the periphery of the electrode. When the electrode is positioned between the pericardium and the heart, the uninsulated surface is disposed to face the pericardium.

In FIG. 3, the three-dimensional tubular electrode 1c is woven from individual fibers 2 or strands 3. By virtue of its flexible fiber construction, the electrode may be compressed along the longitudinal axis of the tube to enlarge its diameter, or may be stretched along that axis as indicated by the double arrows P to reduce its diameter. Accordingly, such an electrode configuration may be adapted to conform closely to the shape of a body organ such as the heart, and to move elastically by expansion and contraction with movements of the organ. This configuration, appropriately shaped, is particularly suited for encompassing a significant area of the surface of the heart for functioning as a defibrillation electrode. When electrode 1c is elongated along the tube axis, its diameter is reduced so that it may be inserted by a puncture needle via a central hole of an introducing catheter for implantation as will be described below. An electrode of tubular configuration may also be introduced into a chamber in the right side of the heart via the superior vena cava as a counter electrode of large effective surface area for cooperation with a patch, fan or tubular electrode external to the heart for defibrillation through the heart tissue disposed between the electrodes. The non-thrombogenic and anti-inflammatory property of the fiber material helps to avoid an early buildup of tissue on the electrode surface which would otherwise tend to reduce the efficiency of the energy transfer during defibrillation. As will be discussed in greater detail below, however, according to the present invention an anti-coagulant agent is applied to the fiber surface of the electrode to improve its capability to prevent thrombosis and connective tissue scar formation.

Figure 5:
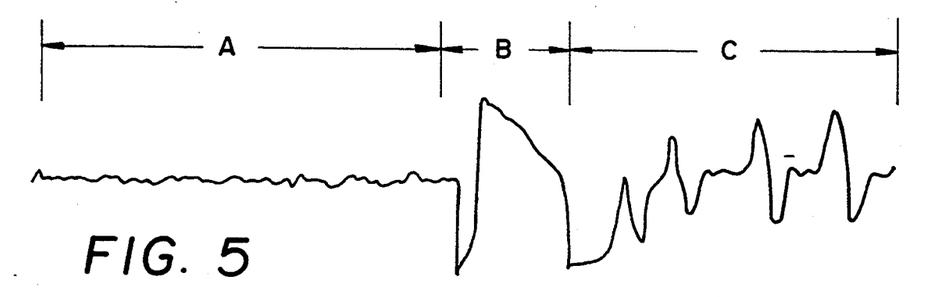
FIG. 5 is an ECG signal waveform illustrating a heart in ventricular fibrillation subjected to defibrillation using a fiber electrode, and return to normal sinus rhythm.

The electrical cardiac signal of a pig heart with induced fibrillation is shown in the waveform chart of FIG. 5, with time plotted along the X-axis. In period A, the heart is in fibrillation as indicated by the random uncoordinated output signal detected by a fiber electrode, of the type shown in FIG. 1, positioned external to the heart. The counter electrode used in defibrillating the heart was a quadripolar endocardial electrode having two electrode points in the atrium and two more in the ventricle at the right side of the heart. In period B an electric shock was applied to the myocardium through the fiber electrode and the counter-electrode. Defibrillation was successful as indicated by return to normal heart rhythm in period C.

Figures 6, 7:
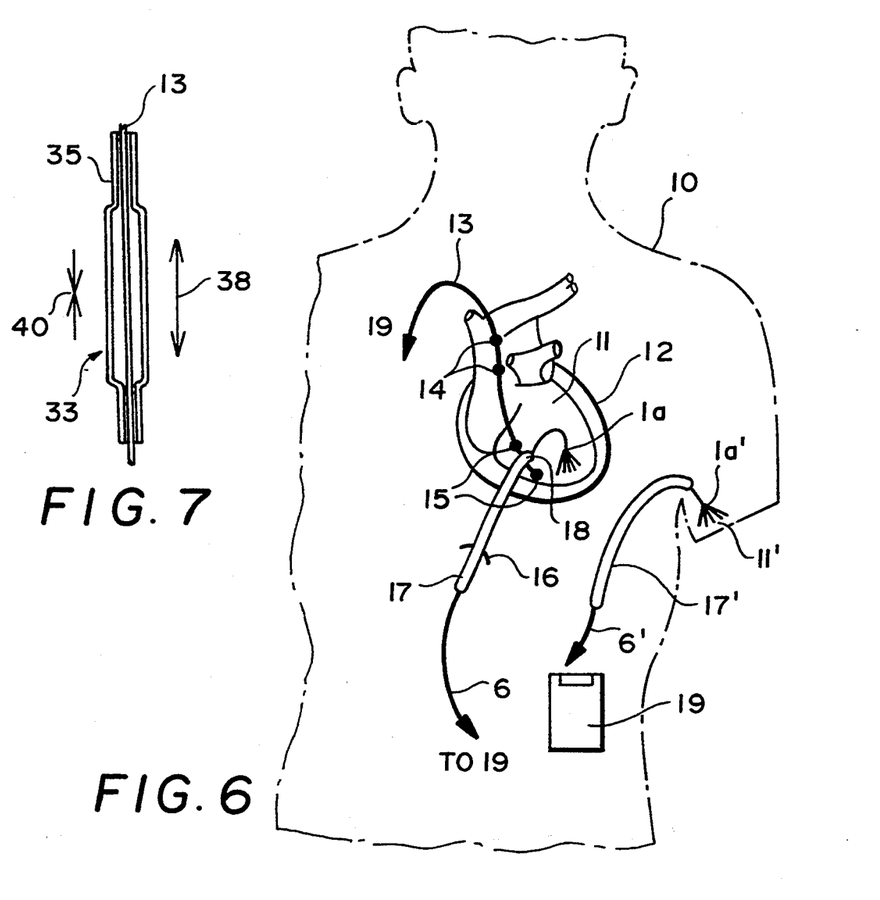
FIG. 6 is a phantom partial view of a patient illustrating the location of the various components of an implanted defibrillator utilizing conductive fiber electrodes.
FIG. 7 is a braided conductive fiber tube electrode coaxially connected in the lead.

FIG. 6 illustrates the positioning of the components of an implanted automatic defibrillator in a patient 10 shown in phantom outline. A lead 13 is introduced intravenously into heart 11 and positioned so that a pair of electrodes 14 on the lead is disposed in the atrium and a second pair of electrodes 15 on the lead is disposed in the ventricle, as counter-electrodes for defibrillation. The external electrode (to the heart) 1a is a fiber bundle of the type shown in FIG. 1, and is connected to lead 6.

As noted above, the fine fiber electrodes of the invention may be, and are especially suited for, implantation at the desired site within the body by puncture surgery with a guide catheter, or by other microsurgical technique. A defibrillation electrode(s) is implanted by first puncturing the chest/abdominal wall, much as one might perform a laparoscopic procedure at that site, and subsequently puncturing the pericardial sac, with a needle. Such a procedure can precisely place the fiber electrode for excitation of tissue when a stimulus is applied, while avoiding the patient trauma of a thoracotomy. After the pericardial sac is punctured, a fine guide wire is introduced into the pericardial space adjacent to the beating heart. The needle is removed and an introducing catheter and dilator are inserted via the guide wire. The fiber bundle or rolled patch electrode is then introduced through the lumen of the catheter, and the catheter is withdrawn to leave the electrode in position between the pericardium and the myocardium for connection via an electrically connected lead to an implanted defibrillator.

If desired, the electrode to be implanted may comprise a plurality of bundles of interwoven isotropically conductive fibers, each of which would be introduced, through the punctures, into the pericardial sac so that the entire array is configured with the fiber bundles substantially equally spaced about the heart. Such an array would be similar to that illustrated in the Offenlegungsschrift DE 40 32 153 A1 of applicant and others in the Federal Republic of Germany, published on Apr. 16, 1992. This type of array, when using the fiber materials described herein, provides a huge effective surface area for energy transfer, compared to the apparent actual surface area of the electrode itself, and allows defibrillation from outside to inside the heart (e.g., by use of an associated endocardial counter-electrode of tubular carbon fiber mesh positioned in the right ventricle), and does so without a need for major invasive surgery. Alternatively, a fiber bundle may be used for the defibrillation electrode, arranged and adapted to fan open as shown in FIG. 1 to provide a large area for electrical contact with the heart.

However, taking into consideration the ease or difficulty of implantation, and the effectiveness of the electrode structure to rapidly effect defibrillation, a carbon fiber tubular coil electrode is the preferred configuration, and will be described in greater detail presently herein.

The patient's ECG may be monitored when the pericardium is punctured, to observe whether and when the puncture needle (which, in that instance, is connected to an ECG amplifier) contacts the heart. Such contact is clearly visible from the reaction of the EGG, and when it occurs the needle is withdrawn slightly to allow introduction of the catheter and the electrode. Alternatively, control may be manifested by using conventional echocardiographic instrumentation, with an ultrasound transmitter placed on the patient's chest to detect initial touching of the heart by the puncture needle.

If the patient's pericardium adheres to the heart, as it would, for example, owing to inflammation or prior open heart surgery, the fiber electrode may be applied directly to the exterior of the pericardial sac by a mediastinoscopy procedure, working under direct visualization by means of endoscopy.

Referring again to FIG. 6, fiber bundle electrode 1a and associated lead 6 are inserted into the target tissue interaction region by the puncture procedure. The puncture needle is inserted into the body 10 at predetermined puncture site 16 between the ribs. The needle is guided into the space between the pericardium 12 and the heart 11 by assistance of X-ray, fluoroscopy or, preferably, endoscopy. Guide catheter 17 is inserted into the body over a guide wire, and an interior dilator is used to expand the passageway through the puncture site 16 and the pericardial sac. The catheter 17 may be bent slightly in its anterior region as shown at 18, to permit easier positioning of the electrode 1a when implanted. After removal of the dilator, fiber electrode 1a with connected lead 6 is inserted through the guide catheter 17 and properly positioned within the pericardial sac for use in defibrillation and sensing functions. The introducer sheaths for the guide catheter may be of known peel-away type for rapid removal. Lead 6 is routed subcutaneously, for example, for electrical connection to automatic defibrillator 19 implanted in the patient's abdominal cavity. Lead 13 incorporates an endocardial counter-electrodes which is also electrically connected to defibrillator 19.

Figure 8A:
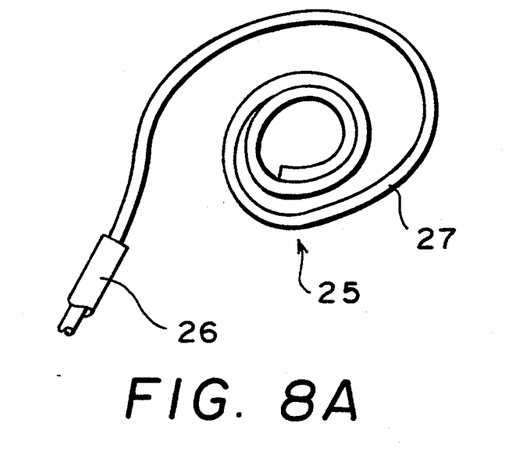
FIGS. 8A and 8B are partial perspective views of a conductive fiber tube coil electrode according to another aspect of the invention.
Figure 8B:
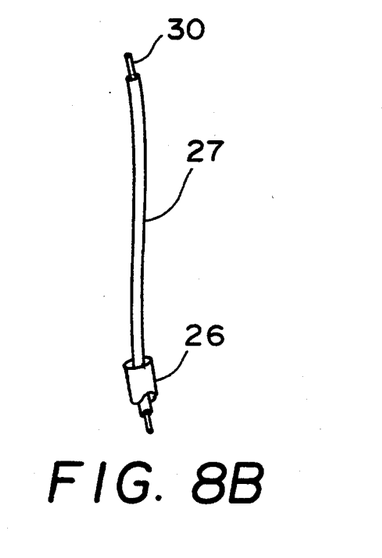

As stated above, the preferred configuration of the fibers of a defibrillation electrode to be positioned external to the heart is a woven tube prestressed to form a flat coil or spiral shape, as shown in FIG. 8A. The flat coil electrode structure 25 is introduced into the pericardial sac adjacent the ventricles by puncture implantation as described above. It is composed of a braided conductive fiber tube 27 which is preformed (prestressed) into the coil or pigtail configuration along a substantial, uninsulated portion of its distal end. Conventional biocompatible insulating material 26 covers the remainder of the tube to its proximal end. The tube is inserted through the puncture in the chest wall using a stiffening wire 30 (FIG. 8B) in the tube's lumen to straighten and stiffen the tube sufficiently to be passed through the puncture. The straightened tube is then guided to and through the pericardial sac by means of an endoscope or other known microsurgical viewing means, into desired position adjacent the ventricular epicardium. The procedure is performed preferably in a series of alternating advancements of the straightened electrode and withdrawals of the stiffening wire, so that the lengthening free, now relaxed end of the electrode is continually returning in greater proportion to its prestressed pigtail shape within the pericardium.

This represents a compromise between ease of placement of the electrode at the selected site, with its elimination of major thoracic surgery and consequent reduction of trauma to the patient, and the probable effectiveness of the electrodes's defibrillation function, compared for example to one or more extensive patch electrodes which might be implanted by a thoracotomy to envelop a major portion of the epicardium or pericardium. The flat coil electrode also provides greater energy efficiency than a fan electrode formed by the free ends of individual fibers of the braided fiber bundle or other easily placeable braided conductive fiber electrode configurations. In any event, however, defibrillation effectiveness and energy efficiency would be determined initially from the results of animal tests.

The flat coil configuration has a relatively larger effective surface area, which is highly desirable, and greater rigidity which enables it to remain more securely in place at the implant site, than a fan electrode configuration. The position-stability of the fan configuration is not as great because the fiber ends are loose, as necessary to allow the electrode to adopt the fan shape, compared to a prestressed flat coil electrode with tubular mesh configuration and an inner electrically insulative material to provide it with mechanical properties sufficient to maintain its shape as a pigtail and remain more securely in place over time.

For precise placement of a polymer fiber electrode by X-ray, fluoroscopy or endoscopy, the fibers may be interspersed with fibers composed of material opaque to radiation of the type employed for viewing the progress of the implantation procedure from a point external to the body. The opaque fibers or strands 8 are interposed among the polymer fibers 2 as shown in the cross-sectional view of FIG. 4. Alternatively, the polymer fibers themselves may be doped or coated with materials impenetrable to such radiant energy. Of course, if the fibers are metallic, whether bare or carbon-coated, they are opaque and readily visualized during the implant procedure. As observed above, coating metallic fibers with carbon material enhances their electrical and biocompatible properties. The carbon is also very useful as an electrochemical carrier for infused antithrombotic, anticoagulant or anti-inflammatory substances.

By use of a tiny endoscope with a diameter of, say, 0.5 to 1 millimeters having 2,000 or more individual glass fibers with a corresponding same number of fiber points at its end, an extremely large field of view is provided by a lens and light source at the end of the instrument. Such instrumentation is sufficiently small to enter the pericardial space, and multiple carbon fibers may be implanted with precision around the heart with the manipulating tools of the instrument. A fluid space of about two to three mm exists between the heart and the pericardial sac, which allows relatively easy entry of the instrument and application of the fibers necessary to provide the defibrillation electrode. In cases where the patient has previously suffered infarction, scarring in the form of adhesions of the pericardial sac to the epicardium will likely be encountered. In those cases, it is necessary to separate the two before the conductive fibers can be inserted into the sac to fully surround the heart. The endoscopic implant procedure is preferred over, say, x-ray viewing using the needle and introducer, having the distinct advantage that bleeding and other trauma can be attended to immediately, as by applying electrical impulses, attaching clips and/or sponging the affected tissue with the associated manipulating tools.

Referring again to FIG. 6 and also to FIG. 7, according to another aspect of the invention, a tubular mesh 33 composed of conductive fibers of the types described herein may be implanted through the vena cava into the right ventricle as an endocardial counter-electrode to one or more epicardial or pericardial patch electrodes. This counter-electrode may be deployed in substantially three-dimensional shape, connected to the distal end of a second current-carrying lead 35 which is coaxial with lead 13. The selective interweaving of the fiber strands of the counter-electrode 33 into its tubular configuration allow it to flex by expansion (shown by arrows 38) and compression (shown by arrows 40) along its longitudinal axis. This permits the tubular electrode to expand axially so that its diameter is reduced for ease of introduction into the heart, and to compress and expand with contraction and relaxation of the heart during each beat to relieve stresses on the electrode structure when positioned within the heart which would otherwise subject it to continuous fatigue and potential fracture. One of the two electrodes may be used for detecting ventricular fibrillation.

This is quite different from previous transvenous electrode systems for defibrillation in which separate right ventricular and vena cava electrodes have been provided for implantation, as well an associated subcutaneous patch. Rather, in accordance with the invention, the vena cava electrode is integral with what is effectively a single coaxial lead without substantially increasing the lead diameter to a size which would preclude its introduction into the vein. According to the invention, in addition to the vena cava electrode and the right ventricular electrode being provided within a single lead, a tip electrode 15 of the same lead is used for sensing, in either bipolar or unipolar electrode configuration.

The braided conductive fiber electrode material may be employed in an alternative lead/electrode assembly to provide a tripolar electrode, which may constitute a configuration similar to that of FIG. 7 except that three individually insulated coaxial conductors—an inner coil, a middle coil, and a third, outer conductor—are used to make electrical connection to respective electrodes of the implantable assembly. The desired result is achieved, in large measure, because the fiber material does not require a large diameter to provide a large surface area—as a consequence of creation of that surface from many tiny woven strands. Thus, a single lead/electrode assembly is capable of providing sensing and pacing as well as defibrillation or other cardioversion (or more broadly, intervention in cardiac activity). The assembly may be fabricated in unipolar, bipolar or even tripolar configuration. A common ground such as the can (metal case) for the implantable device may be used relative to the tip for sensing and pacing, or, preferably, a bipolar configuration may be used to reduce sensitivity to background noise and other interference that could overwhelm or at least impede detection of the desired electrical cardiac signal.

Another important aspect of improved defibrillation electrodes according to the invention is to provide transvenous defibrillation in a way that eliminates the shocks being delivered between an electrode in the right ventricle and another electrode in or substantially in the superior vena cava. Such an arrangement has not proved very reliable for defibrillation because the energy field encompasses little of the septum or the left ventricle of the heart. On the other hand, the approach does recognize the difficulties involved in attempting to implant conventional patch electrodes using conventional highly invasive surgical procedures, and seeks a compromise.

An important consideration is relatively equal distribution of the current field. Theoretically, the distribution would be optimum if the implant site of the electrode were sufficiently remote from the heart, such as a site in the patient's leg—but such positioning would produce much too weak a field because of the great distance from the heart. The most realistic theoretical approach would be to cover the entire outside of the heart, and then defibrillate against an electrode inside the heart. This would also produce a nearly uniform field distribution, with the added advantage of high field strength. Defibrillating from outside to inside the heart is energy efficient not only because it produces the desired virtually equal distribution of the field, but also because the blood in the heart is an excellent conductor.

Nevertheless, it is desirable in view of both surgical and patient considerations to seek to strike a compromise between the theoretical and the practical aspects. In practice, the application of large area electrodes around the heart is a difficult procedure for even the most skilled surgeon, and using conventional techniques, is highly invasive and traumatic to the patient. On the other hand, if the defibrillation threshold can be held as low as approximately five joules, and maintained so that it does not increase significantly over time, it is feasible and a much easier and quite effective approach to use a single transvenous lead according to the invention. This means that both the acute and chronic thresholds should be maintained at extremely low levels. A technique for doing so will be discussed in greater detail presently. Only where the patient has an unusually large heart would it remain desirable to provide additional defibrillating means outside the heart.

Figure 9:
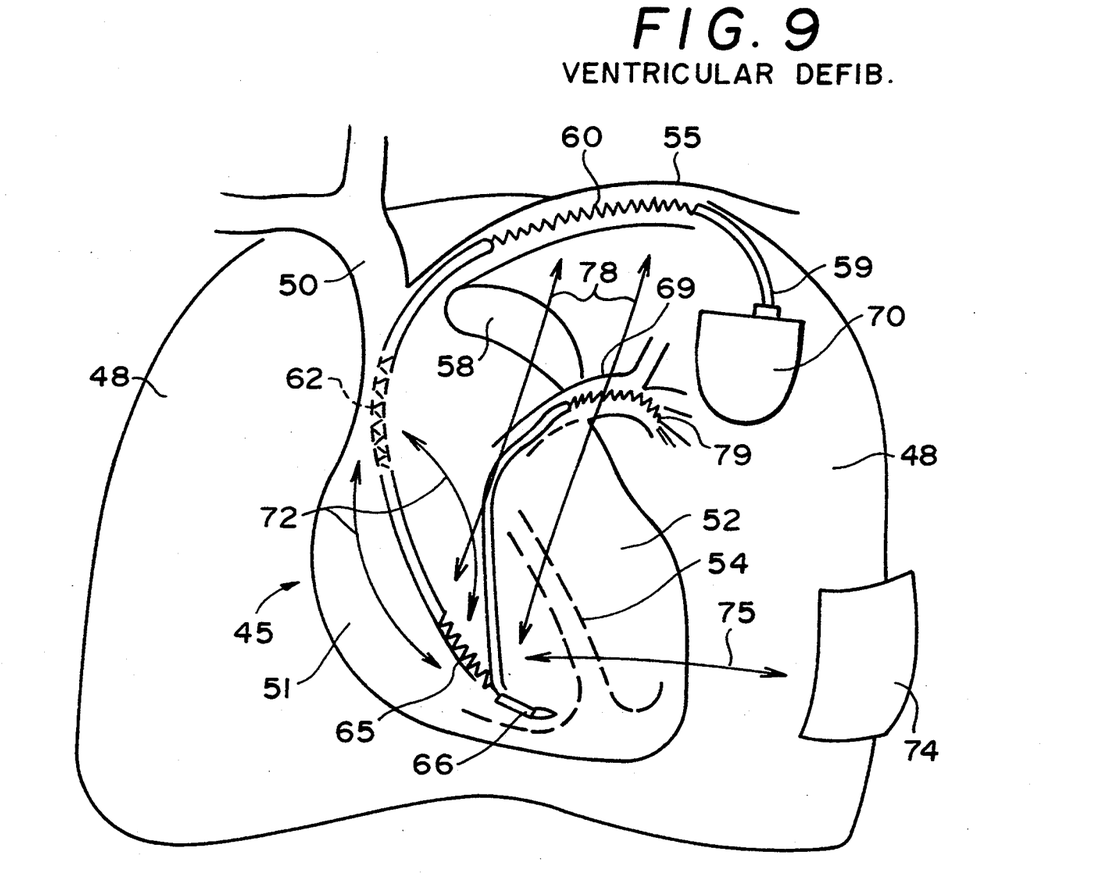
FIGS. 9 and 9A are simplified perspective views of the patient's heart and lungs showing the placement of electrodes when either of two other embodiments of a lead is implanted for ventricular defibrillation or atrial defibrillation respectively.
Figure 9A:
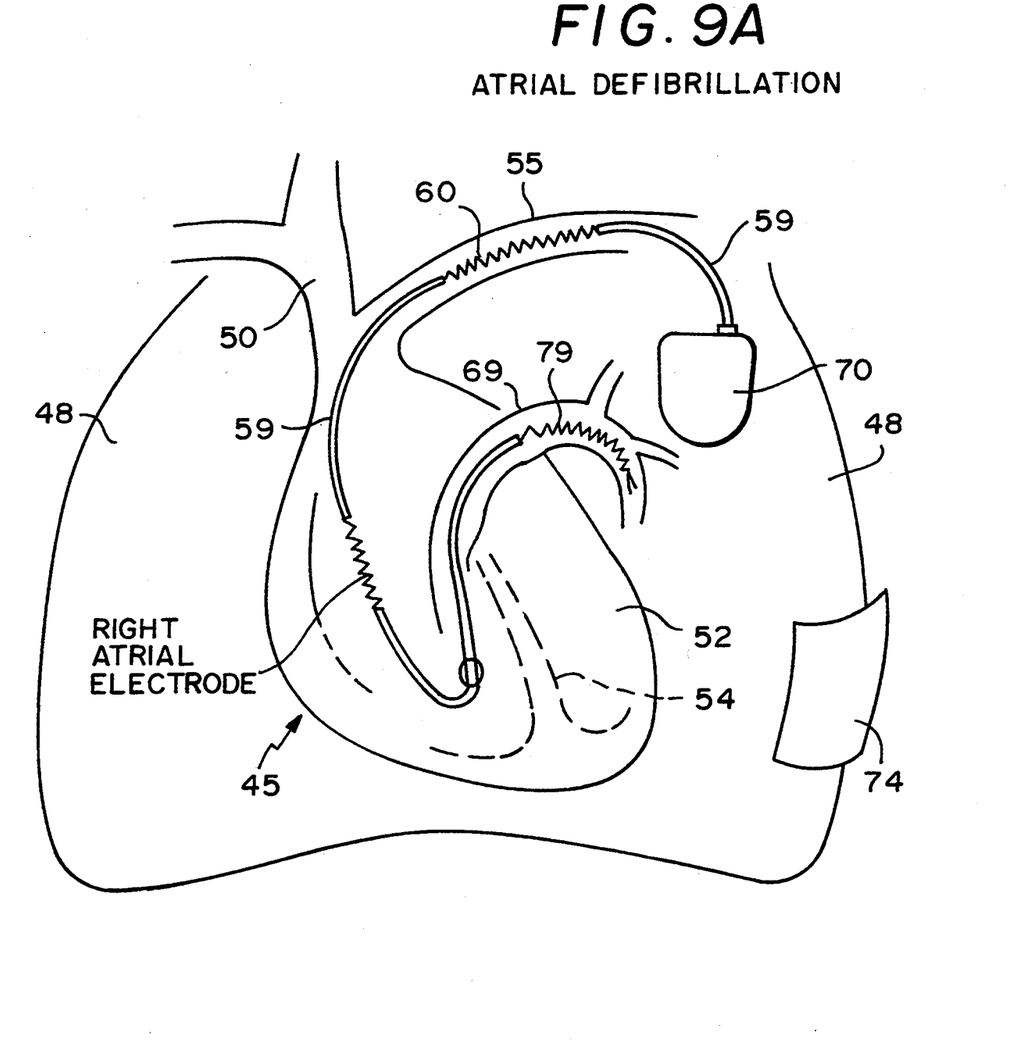

The approach of the present invention of using a single transvenous lead for ventricular defibrillation will be described by reference to FIG. 9. The Figure illustrates, in simplified form, the patient's heart 45 and lungs 48, superior vena cava 50, fight ventricle 51, left ventricle 52, septum 54, and left subclavian vein 55. The aorta 58 and pulmonary artery 59 are generally disposed as indicated. According to the invention, rather than positioning an electrode in the vena cava 50, one pole 60 of single lead 59, either negative or positive (the particular polarity is not critical) is arranged and adapted to be positioned in the left subclavian vein 55. The other pole is provided by electrode 65 which is arranged on the lead to be positioned in the right ventricle when the lead 59 is properly implanted. A pacing and sensing electrode 66 is provided at the distal tip of the lead, and the lead is electrically connected at its proximal end to an implanted defibrillator 70. Actually, device 70 may perform all of the functions appropriate to a cardiac patient, including pacing, anti-tachy cardioversion, and defibrillation.

Alternatively, instead of positioning one electrode pole in the subclavian vein 55, a similar vector (path of the current) can be achieved, but which is even closer to the heart, by placing the electrode (as at 79 in FIG. 9) within the pulmonary artery 59 at the left side of the heart. It is anticipated that the use of these electrode locations in a purely transvenous array may effect defibrillation with better energy efficiency than can be obtained using an epicardial or pericardial patch, quite aside from the consideration of reducing trauma through the transvenous implantation which is far less invasive. The multiple electrode lead may be fabricated according to conventional techniques, subject to using fiber electrodes and the electrical connection techniques discussed herein, the significant aspect here being the arrangement of the electrodes on the lead for positioning and placement relative to the chambers of the heart when the lead is fully implanted.

The desire is to create a considerably higher energy density to the septum and left heart structures than can be achieved with a vena cava electrode such as 62. The latter is shown in phantom purely for the sake of illustration because it is not actually present on a lead fabricated according to this aspect of the invention. If a defibrillating shock or lower level cardioverting impulse is delivered between electrode 62 and the right ventricular (RV) electrode 65, the resulting field tends to be restricted to the right side of the heart, as shown by double-headed arrows 72.

Alternatively, if a subcutaneous patch such as 74 were used for defibrillation together with the RV electrode 65, the field direction would be generally as is illustrated by double-headed arrow 75. The field encompasses a greater portion of the heart structure than the vena cava/RV electrodes arrangement, particularly the ventricular mass. A significant problem here, however, is that the lung has a high specific resistivity, on the order of 1000 ohms per centimeter, which results in a dramatic drop in field strength across that region. Additionally, the heart is anisotropic, i.e., its conductivity and conduction velocity for current flow is considerably greater (about 3.5 times) along its vertical axis, approximately along the septum, than it is along the horizontal axis.

It is quite desirable, then, to provide a field which avoids the drop across the lungs and takes advantage of the anisotropy of the heart. This is precisely the effect achieved with an electrode pole in either the left subclavian vein (as at 60) or in the pulmonary artery (as at 79), in association with an electrode in the right ventricle (as at 65). Here, a strong, substantially uniform field is achieved, with the field direction denoted by double-headed arrows 78, encompassing the left as well as the right side of the heart, and with a strong vertical component.

By use of an electrode arrangement in which one pole is in the right atrium and the other pole is in the pulmonary artery, an optimal energy field is achieved for defibrillation or cardioversion of the atria since the pulmonary artery forms the top of the left atrium. A very practical aspect of this position is that it is much easier to place an electrode within the bloodstream of the pulmonary artery than in the coronary sinus which has heretofore been the selected position for pure atrial defibrillation. This holds true also for external defibrillation or cardioversion of the atria by means of temporary electrodes with the help of external devices. As a consequence of the ideal vector obtained with the right atrium and pulmonary artery positioned electrode poles, an energy level in the range from 0.5 to 2.0 joules is likely to be sufficient for atrial defibrillation, and this low enough to allow the defibrillation to be performed without administering general anesthesia.

Preferably, each of the defibrillating electrodes is fabricated using a braided or mesh conductive fiber structure described above, not only because of its extremely large effective surface area but because it is producible in a tubular structure which will yield to a very narrow size for ease of passage through the vein. For example, the entire three electrode lead of FIG. 9 may be fabricated in a size of 7 to 9 french with three poles. The electrode which serves as the anode (again, which may be either of the two or three defibrillating electrodes) provides the electrical ground reference for the cathode during defibrillation, as well as for the tip electrode 66 during sensing and pacing.

Another important consideration in selecting the electrode material involves the difficulty encountered in sensing following a shock. The shock tends to overwhelm the sensing capability, primarily because of polarization in conventional cardiac electrodes. A further complication is that the tachycardia may have completely different amplitudes from the normal sinus rhythm—by a factor of even perhaps 5 or 10. After a shock is delivered to the heart, not only electrode polarization but the small level of the signal to be sensed may prevent the signal from being detected. The braided carbon fibers, however, are a low polarizing material with the capability to provide reliable sensing of the electrical cardiac signal in these circumstances. If shocks are delivered despite the fact that the patient's heart is beating intrinsically, new tachycardias can be created, with resulting repeated shocking of the patient. This is a serious problem, especially because of automatic gain control typically used in such devices. As the current range is exceeded in either direction, the signal is amplified or suppressed resulting in oversensing and undersensing.

With respect to the important electrical threshold aspect of the invention, it is known that typically, an implanted electrode exhibits an acceptably small acute threshold, so that only a relatively low level of electrical energy is required to produce stimulation or sensing. However, the chronic threshold is usually substantially higher, with the increase occurring only gradually over several weeks as a result of fibrous tissue growth from thrombosis and foreign body reaction. This tends to produce adhesion of the electrode and resultant mechanical stigma that prevents free movement of the electrode. It also reduces energy transfer efficiency across the electron-ion boundary between the electrode and the adjacent blood and tissue. In some cases, the chronic threshold level is so high as to necessitate electrode replacement.

According to an aspect of the invention, heparin, hirudin, steroids or other antithrombotic, anti-inflammatory or anticoagulant substances are incorporated onto the surface of the entire length of the carbon surface of the fibers to prevent clotting and the secondary, post-clotting fibrous tissue growth, so that the fibers will continue to contact blood and excitable tissue over time without undesirable growth of an intervening layer of fibrous connective tissue. Carbon will remain impregnated indefinitely with such substances, with only minor solving into the blood over time.

Such coating or impregnation of the anticoagulant substances may be performed by various different but conventional procedures to achieve bonding of the molecules to the fiber structure, such as an electrochemical process described by Dr. H. Naarman of BASF. Alternative coating techniques include photo-application or pure chemical processes. Whatever process may be used, it is desirable that the anticoagulation agent be kept active in order to achieve satisfactory coating.

A further aspect of the present invention resides in tuning or matching of the electrical characteristics of the output circuit of the defibrillator pulse generator to the characteristics of the lead/electrode system. The characteristics of pulse width, pulse duration, pulse amplitude, pulse shape and current flow generated by the discharge capacitors of the defibrillator should correspond to the low impedance properties of the lead/electrode system, for optimum energy transfer and efficiency. Such matching avoids problems as where a relatively lower impedance lead is utilized with a mesh having a high internal impedance surface. The impedance differences create different energy densities, energy fields and current flow in the two materials, which wastes energy (battery power as well as useful energy delivered for defibrillation).

Matching assists in obtaining the full advantages of the conductive fiber electrode material such as large effective surface area for defibrillation, and allows the integral of defibrillating pulse energy to be more condensed. A high impedance electrode would provide lower current and higher voltage output from the output capacitors of the implanted defibrillator, making the task of the capacitors easier. However, a low impedance electrode permits greater current flow, and for defibrillation the current flow is the more important consideration. Therefore, the waveforms, the discharge characteristics, the rise time, and the duration of the pulse, and where a biphasic waveform is used for defibrillation—the negative and the positive portions of that waveform—are to be matched to the electrode material.

Toward that end, the discharge capacitors are selected for optimal pulse morphology. For example, reduction of the cardioverting or defibrillating pulse width from 4 ms to 2 ms provides an integral of current flow which is higher and shorter than for the wider pulse. Although the same total energy is applied—say, five joules—it is delivered in a condensed form which is more likely to achieve defibrillation. This requires the electrical properties of the electrode to be matched to the output circuit characteristics of the defibrillator. The low impedance structure of a braided carbon fiber material, with its very large effective surface area, allows rapid delivery of desired energy density for maximum current in the shortest possible time.

Matching of the defibrillator and the electrode is optimally achieved by animal testing, to determine the highest efficiency. Different pulse waveforms are applied to the implanted electrode, and the performance of each is evaluated to determine which configuration provides the best result.

Although certain preferred embodiments of the electrode and methods of fabrication and implantation thereof have been described herein, it will be apparent to those skilled in the art from the foregoing description, that variations and modifications of the disclosed embodiments and methods may be made without departing from the true spirit and scope of the invention. Accordingly, it is intended that the invention shall be limited only to the extent required by the appended claims and the rules and principles of applicable law.

What is claimed is:

1. A method for surgical implantation of an electrode in a patient for use in defibrillating the patient's heart, which comprises:
    selecting an electrical lead having at its distal end a defibrillation electrode composed of a multiplicity of fine, elongate, juxtaposed, individual, flexible conductive fibers each having an uncoated, relatively smooth surface layer of carbon derivative of substantially uniform thickness along substantially an entire length of each of said fibers to provide an overall electrode effective electrical surface area which is a cumulative effect of each surface area of the individual fibers and considerably greater than the geometric surface area of the electrode, for implantation in the patient's body;
    puncturing a preselected site in the chest/abdominal wall of the patient for insertion of the flexible fiber electrode and lead therein; and
    inserting the flexible fiber electrode and lead through the puncture site, and maneuvering the inserted fiber electrode into position within the patient's body to encompass a portion of the ventricular mass of the heart for electrical stimulation of the ventricles when the electrode is energized, while viewing the maneuvering externally on a visual internal body scanner.

2. The method of claim 1, wherein the viewing is performed by endoscopy.

3. The method of claim 1, wherein the defibrillation electrode is a tube composed of interwoven fibers prestressed to assume a flat coiled shape when unrestrained, including maneuvering the tube into position with a straightening wire therein, and withdrawing the straightening wire after the electrode is properly positioned to allow the defibrillation electrode to return to its flat coiled shape at a preselected location.

4. The method of claim 3, including positioning the defibrillation electrode within the pericardial sac.

5. The method of claim 4, further including puncturing the pericardial sac for insertion of the defibrillating electrode therein while the straightening wire is within the tube.

6. The method of claim 1, including
    selecting said fiber electrode formed from a bundle of generally interwoven fibers secured together at one end and free of one another at the other end, so that each fiber has a considerable length of its free end unconnected to the adjacent corresponding free end of the other fibers in the bundle, whereby to form a fan-shaped electrode when positioned adjacent the heart.

7. The method of claim 1, including
    selecting said fiber electrode formed from conductive fibers each having a carbon surface, and having the carbon surface of the fibers impregnated with an antithrombin or antiinflammatory substance prior to implantation, to inhibit fibrotic growth along substantially an entire surface of the electrode which is exposed to blood and tissue when implanted in the patient's body.

8. The method of claim 1, including
    selecting said fiber electrode formed from a multiplicity of woven strands of tiny individual elongate uninsulated fibers composed of substantially isotropic electrically conductive material electrically connected to said lead, so that the electrode provides an electron-ion interface with blood and/or body tissue for efficient transfer of electrical energy along an entire substantial length of uninsulated surface of the fibers, in which the surface of the fibers cumulatively presents an effective electrical surface area considerably greater than the actual geometric surface area calculated from the linear dimensions of the electrode.

9. The method of claim 8, including
    selecting said electrode in which the electrode fibers have a carbon surface impregnated with a substance which acts to suppress the formation of fibrotic connective tissue over time at an exposed surface of the electrode when implanted in the patient's body.

10. A method for defibrillating the heart of a patient, comprising the steps of:
    implanting in the patient an electrical lead having a proximal end and a distal end, and having at its distal end a flexible electrode composed of conductive fibers each having an uncoated carbon surface, and in which the carbon surface of substantially each of the fibers is impregnated to bond with molecules of a substance selected to inhibit growth of fibrotic connective tissue at each impregnated surface of the electrode exposed to blood and tissue when implanted in the patient's body, positioning the implanted electrode relative to the patient's heart for use in defibrillating the heart when the electrode is energized with a defibrillating electrical waveform, and electrically connecting the proximal end of the lead to a source of said defibrillating electrical waveform.

11. The method of claim 10, including selecting a flexible electrode in which the growth-inhibiting substance is heparin.

12. The method of claim 10, including selecting a flexible electrode in which the growth-inhibiting substance is hirudin.

13. The method of claim 10, including selecting a flexible electrode in which the growth-inhibiting substance is a steroid drug.

14. The method of claim 10, including arranging the fibers of the flexible electrode in an array to encompass a portion of the epicardial surface of the patient's heart adjacent a heart chamber to be defibrillated, when the electrode is implanted.

15. The method of claim 14, wherein the flexible electrode is a tubular configuration of interwoven isotropic conductive fiber strands, and including prestressing the configuration to assume a flat coiled shape when unrestrained.

16. A lead assembly for use in defibrillating the heart of a patient in which the lead assembly is to be implanted, comprising:

an electrically conductive lead wire having a proximal end and a distal end, a flexible stimulating electrode composed of a multiplicity of fine, elongate, electrically conductive fibers each having an uncoated carbon surface of substantially uniform thickness over substantially its entire length, the electrode being electrically connected to the distal end of the lead wire for implantation in the patient's body and adapted, when the electrode is implanted at a selected site in the patient's body and the proximal end of the lead wire is connected to a defibrillator, to accept electrical energization of sufficient magnitude to defibrillate the heart, and a substance incorporated into the carbon surface of the fibers of the electrode in a molecular bond with and not a coating of the carbon surface to impede the growth of fibrotic connective tissue at a surface of the electrode exposed to blood and tissue when implanted in the patient's body.

17. The lead assembly of claim 16, wherein said substance is heparin.

18. The lead assembly of claim 16, wherein said substance is hirudin.

19. The lead assembly of claim 16, wherein said substance is a steroid.

20. An implantable lead for use in cardioversion or defibrillation of a human heart, comprising:

an elongate electrical conductor, and an electrode electrically connected to the conductor, the electrode including:

a multiplicity of juxtaposed, fine, uninsulated, elongate, individual, flexible metallic fibers each of a diameter considerably smaller than its length, and of sufficient number to provide an overall effective electrically conductive surface area formed by individual surfaces of the multiplicity of fibers considerably greater than the outer geometrical surface area encompassing the electrode and capable of being non-destructively energized by electrical waveforms of magnitude and other characteristics suitable to defibrillate a human heart, and maintaining means for holding the multiplicity of fibers in a flexible configuration having a shape and size selected according to an intended location of the electrode when the lead is implanted for use in cardioversion or defibrillation of the heart.

21. The implantable lead of claim 20, wherein:
said maintaining means comprises the fibers themselves interwoven into said shape and size.

22. The implantable lead of claim 20, wherein:
the fibers have a surface layer composed of an electrically conductive carbon derivative.

23. The implantable lead of claim 27, wherein:
said surface layers is impregnated with a substance for impeding at least one of thrombosis, inflammation, and coagulation at the electrode surface when the lead is implanted.

24. The implantable lead of claim 20, wherein:
the fibers are composed of a platinum iridium alloy.

25. The implantable lead of claim 24, wherein:
each fiber is a strand of said platinum iridium alloy of approximately 27 microns in diameter.

26. The implantable lead of claim 25, wherein:
said fibers are arranged in multi-strand bundles of nine strands each, and a plurality of said bundles are braided to form said electrode.

27. An implantable lead for use in cardioversion or defibrillation of a human heart, comprising:

an elongate electrical conductor, and an electrode electrically connected to the conductor, the electrode including:

a multiplicity of individual, flexible metallic fibers each of a diameter considerably smaller than its length, each fiber having a surface layer composed of a substantially isotropic electrically conductive carbon derivative, to provide an overall effective electrically conductive surface area formed by the individual surfaces of the multiplicity of fibers considerably greater than the outer geometrical surface area encompassing the electrode, and maintaining means for holding the multiplicity of fibers in a flexible configuration having a shape and size selected according to an intended location of the electrode when the lead is implanted for use in cardioversion or defibrillation of the heart.

28. The implantable lead of claim 27, wherein:
said maintaining means comprises the fibers themselves interwoven into said shape and size.

29. The implantable lead of claim 27, wherein:
said surface layer includes means for impeding at least one of thrombosis, inflammation, and coagulation at the electrode surface when the lead is implanted.

30. The implantable lead of claim 27, wherein:
the fibers are composed of a platinum iridium alloy.

31. The implantable lead of claim 301, wherein:
said fibers are arranged in multi-strand bundles, each strand being composed of said alloy and having a diameter in a range from about 10 to about 30 microns, and a plurality of said bundles are braided to form said electrode.

* * * * *